United States Patent

Lee et al.

[11] 4,178,253
[45] Dec. 11, 1979

[54] CORROSION INHIBITED LUBRICANT COMPOSITIONS

[75] Inventors: Peter I. Lee, Prestwood; Brian Holt, Stretford, both of England

[73] Assignee: Ciba-Geigy Corporation, Ardsley, N.Y.

[21] Appl. No.: 892,711

[22] Filed: Apr. 3, 1978

[30] Foreign Application Priority Data

Apr. 5, 1977 [GB] United Kingdom ............... 14357/77

[51] Int. Cl.$^2$ ............................................. C10M 1/38
[52] U.S. Cl. ..................................... 252/47; 546/210; 546/276; 548/130; 548/169; 548/263; 548/265; 548/327; 548/329; 252/47.5; 252/391; 544/209
[58] Field of Search ........................ 252/47, 391, 47.5; 260/302 SD, 302 R, 308 R, 308 D, 306.5, 306.6 R; 544/209

[56] References Cited

U.S. PATENT DOCUMENTS

| | | |
|---|---|---|
| 2,618,603 | 11/1952 | Schaeffer ............................. 252/47 X |
| 2,618,605 | 11/1952 | Schaeffer ............................. 252/47 X |
| 2,719,126 | 9/1955 | Fields et al. ......................... 252/47 X |
| 3,591,500 | 7/1971 | Sullivan .................................. 252/47 |
| 3,689,501 | 9/1972 | Weaver et al. ............. 260/306.6 R X |
| 3,701,784 | 10/1972 | Seidel et al. ..................... 260/308 R |
| 3,775,321 | 11/1973 | Turnquest et al. ................ 252/58 X |
| 3,896,050 | 7/1975 | White ................................. 252/47 X |
| 3,914,241 | 10/1975 | Elliott et al. ................ 252/32.7 E X |
| 3,969,353 | 7/1976 | Schwarze et al. ............... 544/209 X |
| 4,038,197 | 7/1977 | Caspari .............................. 252/47 X |

FOREIGN PATENT DOCUMENTS 46-098159 4/1971 Japan .

*Primary Examiner*—Delbert E. Gantz
*Assistant Examiner*—Andrew Metz
*Attorney, Agent, or Firm*—Luther A. R. Hall

[57] ABSTRACT

A lubricating oil composition comprising 0.001% to 10%, based on the total lubricating composition, of a compound of formula I:

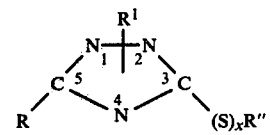

wherein x is an integer from 1 to 25; R, R$^1$ and R'' are the same or different and each is hydrogen, an optionally substituted straight- or branched-chain alkyl residue having from 1 to 20 carbon atoms, an alkenyl or alkynyl residue having from 2 to 12 carbon atoms, an optionally substituted cycloalkyl residue having from 3 to 12 carbon atoms, an optionally substituted aryl residue having from 6 to 10 carbon atoms, an optionally substituted aralkenyl or aralkynyl residue each having from 8 to 12 carbon atoms, an optionally substituted aralkyl residue having from 7 to 20 carbon atoms or an optionally substituted heterocyclic residue having from 3 to 10 ring members, an alkylene residue having from 2 to 12 carbon atoms, a cycloalkylene residue having from 5 to 12 carbon atoms or an arylene residue having from 6 to 10 carbon atoms; or R is the group -(S)$_x$R'' and when R and R' are different from R'', R'' can also be one of the following residues:

(a) a residue of formula:

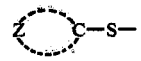

II wherein Z is the atom grouping necessary to complete, with the carbon atom, a heterocyclic ring, or (b) a quaternary ammonium cation derived from the reaction of a compound of formula I, wherein R'' is hydrogen, with ammonia or an amine; and when R'' is hydrogen, R or R' can also be an organic residue which links two triazole residues of formula I, wherein R' is in the 4-position.

6 Claims, No Drawings

CORROSION INHIBITED LUBRICANT COMPOSITIONS

The present invention relates to chemical compositions and, in particular, to lubricant compositions comprising 1,2,4-triazole compounds.

The incorporation of extreme pressure/anti-wear additives into lubricating oil basestocks, whilst preventing excessive wear, can lead to corrosion. This is particularly the case when non-ferrous metals e.g. copper are present.

We have now developed certain additives which, when incorporated into lubricating oils, inhibit corrosion caused by sulphur and phosphorus/sulphur extreme pressure and antiwear additives.

The present invention provides a lubricating oil composition comprising 0.001 percent to 10 percent, preferably 0.01 percent to 5 percent, most preferably 0.1 percent to 2 percent by weight, based on the total lubricating composition, of a compound of formula I:

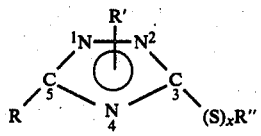

wherein x is an integer from 1 to 25, preferably 1 to 10, more preferably 1 to 4; R,R', R" are the same or different and each is hydrogen, an optionally substituted straight or branched alkyl residue having from 1 to 20 carbon atoms, an alkenyl or alkynyl residue having from 2 to 12 carbon atoms, an optionally substituted cycloalkyl residue having from 3 to 12 carbon atoms, an optionally substituted aryl residue having from 6 to 10 carbon atoms, an optionally substituted aralkenyl or aralkynyl residue having from 8 to 12 carbon atoms, an optionally substituted aralkyl residue having from 7 to 20 carbon atoms or an optionally substituted heterocyclic residue having 3 to 10 ring members, an alkylene residue having from 2 to 12 carbon atoms, a cycloalkylene residue having from 5 to 12 carbon atoms or an arylene residue having from 6 to 10 carbon atoms; or R is a group $-(S)_xR''$ and when R and R' are different to R", and especially when x is 1, then R" may also be one of the following residues:
(a) a residue of formula II

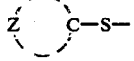

wherein Z is the atom grouping necessary to complete, with the carbon atom, a heterocyclic ring, or
(b) a quaternary ammonium cation derived from the reaction of a compound of formula I, when R" is hydrogen, with ammonia or an amine; and when R" is hydrogen, R or R' can also be an organic residue which links two triazole residues of formula I, wherein R' is in the 4-position. The "floating" substituent R' may be in the 1-, 2-, or 4-position. Examples of residues of formula II are:

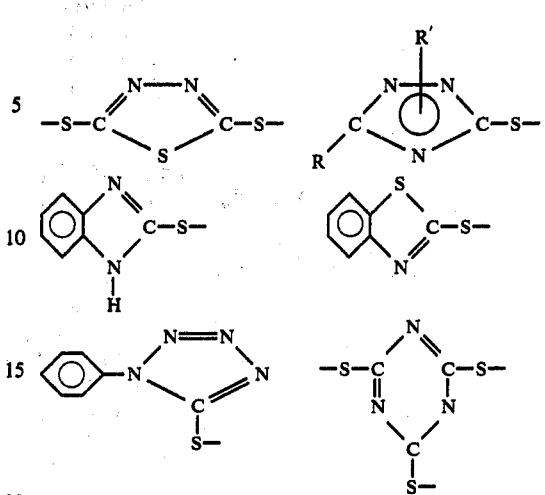

Examples of suitable amines for use in reaction with a compound of formula I are ammonia, ethylamine, di-n-butylamine, t-octylamine, n-decylamine, di-n-decylamine, t-dodecylamine, t-octadecylamine, n-docosanylamine. Examples of the groups, R, R', R" are, apart from hydrogen, methyl, ethyl, n-propyl, isopropyl, n-butyl, isobutyl, secbutyl, n-pentyl, 2-methylbutyl, n-hexyl, 2-methylpentyl, n-heptyl, n-octyl, 2-ethylhexyl, 1:1:3:3-tetramethylbutyl, nonyl, n-decyl, n-undecyl, n-dodecyl, 1:1:3:3:5:5-hexylmethylhexyl, n-tetradecyl, n-hexadecyl, n-octyldecyl, eicosyl; vinyl, crotyl, α-methylvinyl, 1-hexenyl, 2-octenyl, 1-decenyl 1-dodecenyl, oleyl, propargyl, methylpropargyl; cyclopropyl, cyclobutyl, cyclopentyl, cyclohexyl, 1-methylcyclohexyl, 4-methylcyclohexyl, cyclooctyl, cyclodecyl, cyclododecyl; phenyl, p-tolyl, m-ethylphenyl, p-isopropylphenyl, o-isopropylphenyl, p-t-butylphenyl, p-1:1:3:3-tetramethylbutylphenyl, o-1-methylheptylphenyl, p-nonylphenyl, p-dodecylphenyl, naphthyl, 2-methyl naphthyl; benzyl, β-phenylethyl, α-methylbenzyl, α,α-dimethylbenzyl, naphthylmethyl; cinnamyl (β-phenylvinyl), β-phenyl propargyl; pyridyl and piperidyl residues.

The cycloalkyl, aryl, aralkyl, aralkenyl, aralkynyl or heterocyclic substituents R, R' and R" may be each unsubstituted or substituted by one or more of the following substituent groups: straight or branched alkyl groups containing from 1 to 12 carbon atoms which may themselves be optionally substituted by halogen atoms; alkoxy groups containing from 1 to 12 carbon atoms; alkylthio groups containing from 1 to 18 carbon atoms; alkyl or dialkylamino groups containing from 1 to 24 carbon atoms; hydroxy groups; cyano groups; or any combination thereof.

When R, R' and R" are straight or branched alkyl groups they may be optionally substituted by one or more halogen atoms or alkoxy groups containing from 1 to 12 carbon atoms.

Examples of such substituted alkyl groups R, R' and R" are chloromethyl, bromomethyl, chloroethyl, bromopropyl, methoxy methyl, ethoxyethyl, chlorobutyl, bromohexyl, chlorooctyl, chlorodecyl, chlorododecyl, chlorotetradecyl, chlorohexadecyl, chlorooctadecyl and chloroeicosyl.

When one or more of R, R' and R" are alkylene residues, they may be e.g. an ethylene-1,2-, propylene-1,3-, butylene-1,4-, pentylene-1,5-, hexylene-1,6-, heptylene-1,7-, octylene-1,8-, nonylene-1,9-, decylene-1,10-, undecylene-1,11- or dodecylene-1,12- residue. Cycloalkylene residues R, R' and R" are e.g. 1,2-cyclopentylene, 1,4-cycloheptylene, 1,4-cyclooctylene and 1,4-cyclododecylene. Arylene residues R, R' and R" are e.g. 1,2-phenylene, 1,3-phenylene, 1,4-phenylene, 1,4-naphthylene and 2,3-naphthylene residues.

Some of the compounds of formula I are new, in particular those wherein x is greater than 1; and as such these compounds (of formula IA) form one aspect of the present invention.

The lubricating oil component of the composition of the present invention may be a mineral oil, a synthetic oil or any mixture of such oils. Mineral oils are preferred and examples of these include paraffinic hydrocarbon oils, e.g. an SAE 20 paraffinic mineral oil having a viscosity of 8.0 centistokes at 99° C.; "150 Solvent Neutral" a solvent refined neutral mineral oil having a viscosity of 5.34 centistokes at 99° C.; and "Solvent Brightstocks", a high-boiling residue from the process of refining mineral oil, and having a viscosity of 32.3 centistokes at 99° C.

Synthetic lubricating oils which may be present include simple di-, tri- and tetraesters, complex esters and polyesters derived from carboxylic acids and hydroxy compounds. Preferred are dicarboxylic acid esters of formula:

$$R^6\text{—OOC—alkylene—COOR}^7$$

wherein "alkylene" denotes an alkylene residue having from 2 to 14 carbon atoms and $R^6$ and $R^7$ are the same or different and each is an alkyl group having from 6 to 18 carbon atoms.

Triesters which are of use as lubricating oil basestocks may be for example those derived from trimethylolpropane and $C_6$–$C_{18}$ monocarboxylic acids or mixtures thereof, or trimellitates derived from trimellitic acid (anhydride) and 6–18C alcohols. Suitable tetraesters include those derived from pentaerythritol and a $C_6$–$C_{18}$ monocarboxylic acid or mixtures thereof.

Complex esters suitable for use as components of the compositions of the present invention are those derived from monobasic acids, dibasic acids and polyhydric alcohols, for instance the complex ester derived from trimethylol propane, caprylic acid and sebacic acid.

Suitable polyesters are those derived from an aliphatic dicarboxylic acid having from 4 to 14 carbon atoms and at least one aliphatic dihydric alcohol having from 3 to 12 carbon atoms, e.g. those derived from azelaic acid or sebacic acid and 2,2,4-trimethylhexane-1,6-diol.

The lubricating oils may also be polyglycols, and polyglycolethers, polyphenyl ethers, synthetic hydrocarbons, polysiloxanes, silicates or phosphates.

The lubricating oil compositions of the invention may, if desired, contain in addition other additives which are conventionally added to improve the properties thereof, such as antioxidants, metal passivators, rust inhibitors, viscosity index improvers/pour point depressants, dispersants/detergents, discolouration and corrosion inhibitors and extreme pressure/antiwear additives.

Examples of antioxidants are:
(a) Alkylated and non-alkylated aromatic amines and mixtures thereof, for example dioctyldiphenylamine; mono-t-octyl-phenyl-α and β-naphthylamines; dioctylphenothiazine; phenyl-α-naphthylamine; phenothiazine; N,N'-di-sec.butyl p-phenylenediamine.
(b) Hindered phenols, for example, 2,6-ditertiarybutyl-p-cresol; 4,4'-methylene-bis-(2,6-di-ti-butylphenol); 2,4,6-triisopropylphenol; 2,2'-thio-bis-(4-methyl-6-tertburylphenol);
(c) Alkyl, aryl or alkaryl phosphites, for example, triphenylphosphite; trinonylphosphite; diphenyldecylphosphite;
(d) Esters of thiodipropionic acid, for example, dilaurylthiodipropionate.
(e) Salts of dithiocarbamic and dithiophosphoric acids, for example, antimony diamyldithiocarbamate, zinc diamyldithiophosphate.
(f) Metal salts, complexes of organic chelating agents, for example, copper bis-(trifluoroacetylacetonates), copper phthalocyanines, tributyl ester of EDTA monosodium salt.
(g) Free radical antioxidants, for example, nitroxides, etc.
(h) Combinations of two or more antioxidants from any of the above sections, for example, an alkylated amine and a hindered phenol.

Examples of metal passivators are:
(a) For copper, for example, 1,2,4-triazoles, benzotriazole, 5,5'-methylene-bisbenzotriazole, tetrahydrobenzotriazole or their derivatives, 2,5-dimercaptothiadiazole and derivatives, salicylidenepropylenediamine, salts of salicylaminoguanidine.
(b) For magnesium, for example, pyridylamines.
(c) For lead, for example, sebacic acid, quinizarin, propyl gallate.
(d) Combinations of two or more of the above additives.

Examples of rust inhibitors are:
(a) Organic acids, and their esters, metal salts, anhydrides, for example, N-oleoyl sarcosine, sorbitan mono-oleate, lead naphthenate, dodecenylsuccinic anhydride.
(b) Nitrogen containing materials, for example:
   (i) primary, secondary or tertiary aliphatic or cycloaliphatic amines and amine salts of organic and inorganic acids, for example, morpholine, stearylamine, triethanolamine caprylate;
   (ii) heterocyclic compounds, for example, imidazolines, oxazolines.
(c) Phosphorus containing materials, for example, inorganic phosphates, phosphonic acids, amine phosphates.
(d) Sulphur containing materials, for example, barium dinonylnaphthalene sulphonates.
(e) Combinations of two or more of the above additives.

Examples of viscosity index improvers/pour point depressants are, for example:
polyacrylates, polybutenes, polyvinyl pyrrolidones.

Examples of dispersant/detergents are, for example:
metal sulphonates (Ca,Ba,Mg) and phenates, polybutenyl succinimides.

Examples of extreme pressure/antiwear additives are:
sulphur and/or phosphorus and/or halogen containing materials, for example, sulphurised sperm oil, sulphurised olefins, polysulphides, zinc dialkyl or diaryl phosphorodithioates, tritolylphosphate, chlorinated paraffins, triphenylphosphorothionate. Olefins treated with $P_2S_5$ and terpenes.

The present invention also provides a process of producing compositions of lubricating oils comprising a compound having the formula I which comprises admixing the lubricating oil with the compound having the formula I.

The compounds of formula I wherein R" is hydrogen may be produced by heating alkaline solutions of the corresponding thiosemicarbazide or bis(thiosemicarbazide).

For instance, the reactants may be heated in an aqueous medium at the reflux temperature of the reaction mixture, and the compound of formula IA, may be optionally isolated by precipitation with an acid, then filtered off and dried.

Compounds of formula IA, wherein x is 2, R″ is a group other than hydrogen and R′ is in the 2- or 4-position, may be produced by cyclising the corresponding thiosemicarbazide; followed by reaction of a sulphenyl halide or bis(sulphenyl halide) with the alkali metal salt of the mercapto-1,2,4-triazole. Alternatively, a mercapto compound of formula R″SH may be reacted with a sulphenyl halide produced by halogenation of the mercapto-1,2,4-triazole. Compounds of formula IA, wherein x is 1 and R″ is a group other than hydrogen and R′ is in the 2- or 4-position, may be prepared by heating the mercapto-1,2,4-triazole (prepared by cyclisation of the thiosemicarbazide) with an organic halide or dihalide. Preferably, the reaction is effected in an organic solvent, e.g. a lower aliphatic alcohol such as ethanol. Alternatively the alkali metal salt of the mercapto-1,2,4-triazole may be reacted with an organic halide or dihalide in a lower aliphatic alcohol such as ethanol.

Bis-(thiosemicarbazides) may be cyclised to produce compounds of formula I wherein R″ is hydrogen and R or R′ an organic residue which links two 1,2,4-triazole rings and R′ is in the 4-position. In these reactions, R or R′ may be alkylene, cycloalkylene or arylene residues.

To produce compounds of formula IA, wherein x is 1 or 2 and R″ is an organic residue which links two 1,2,4-triazole rings through the sulphur atom(s), mercaptotriazoles may be reacted with organic dihalides, or their alkali metal salts with organic dihalides or with bis(sulphenylhalides).

Compounds of formula IA, wherein x is 1 and R″ is hydrogen and R′ is in the 1-position may be prepared by heating an acyl- or aroylthiocarbaminyl thioglycollic ester with an organic hydrazine. Preferably, the reaction is effected in an organic solvent, e.g. a lower aliphatic alcohol such as ethanol. The resulting mercaptotriazole may be converted to compounds of formula IA, in which R″ is a group other than hydrogen and x is either 1 or 2, as previously described.

Compounds of formula IA in which x is 1 and R″ is a group other than hydrogen and R′ is in the 1-position may also be prepared by heating a dithiocarbamate of formula III with an organic hydrazine:

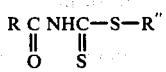     III

Preferably, the reaction is effected in an organic solvent, e.g. a lower aliphatic alcohol such as ethanol.

Alkylammonium salts of compounds of formula IA when R″ is hydrogen may be produced by heating the compound of formula IA in the presence of the amine.

Specific examples of compounds of formula I or IA are:
3-mercapto-1,2,4-triazole
3-(ethylthio)-4-methyl-1,2,4-triazole
3-(t-octyldithio)-4-n-propyl-1,2,4-triazole
3-(sec.-dodecylthio)-4-sec.-butyl-1,2,4-triazole
3-(n-octadecyldithio)-4-n-hexyl-1,2,4-triazole
3-(benzylthio)-4-t-octyl-1,2,4-triazole
3-(cyclohexyldithio)-4-n-dodecyl-1,2,4-triazole
3-(cyclohexylthio)-4-n-octadecyl-1,2,4-triazole
2-methyl-3-(n-dodecylthio)-1,2,4-triazole
3-(ethyldithio)-5-methyl-1,2,4-triazole
3-(n-octylthio)-5-ethyl-1,2,4-triazole
3-(n-dodecyldithio)-5-t-butyl-1,2,4-triazole
3-(sec.-dodecylthio)-5-(2,2-dimethylpropyl)-1,2,4-triazole
3-(n-octadecyldithio)-5-n-hexyl-1,2,4-triazole
3-(benzyldithio)-5-sec.-heptyl-1,2,4-triazole
3-mercapto-5-n-nonyl-1,2,4-triazole
3-(cyclohexylthio)-5-n-tridecyl-1,2,4-triazole
3-(benzylthio)-5-n-pentadecyl-1,2,4-triazole
3-(t-octyldithio)-5-n-heptadecyl-1,2,4-triazole
3-(ethylthio)-4,5-dimethyl-1,2,4-triazole
3-(t-octyldithio)-4-methyl-5-ethyl-1,2,4-triazole
3-mercapto-4-methyl-5-(2,2-dimethylpropyl)-1,2,4-triazole
3-(sec.-dodecylthio)-4-methyl-5-n-nonyl-1,2,4-triazole
3-(n-octadecyldithio)-4-methyl-5-n-heptadecyl-1,2,4-triazole
3-(benzylthio)-4-sec.-butyl-5-methyl-1,2,4-triazole
3-(cyclohexyldithio)-4-sec.-butyl-5-t-butyl-1,2,4-triazole
3-mercapto-4-n-sec.-butyl-5-n-hexyl-1,2,4-triazole
3-(ethyldithio)-4-sec.-butyl-5-n-tridecyl-1,2,4-triazole
3-(n-octylthio)-4-sec.-butyl-5-n-pentadecyl-1,2,4-triazole
3-mercapto-4-t-octyl-5-methyl-1,2,4-triazole
3-(n-dodecylthio)-4-t-octyl-5-ethyl-1,2,4-triazole
3-(n-octadecylthio)-4-t-octyl-5-t-butyl-1,2,4-triazole
3-(benzyldithio)-t-4-octyl-5-n-heptyl-1,2,4-triazole
3-(cyclohexylthio)-4-t-octyl-5-n-tridecyl-1,2,4-triazole
3-(t-octylthio)-4-t-octyl-5-n-heptadecyl-1,2,4-triazole
3-mercapto-4-n-octadecyl-5-methyl-1,2,4-triazole
3-(benzylthio)-4-n-octadecyl-5-ethyl-1,2,4-triazole
3-(cyclohexyldithio)-4-n-octadecyl-5-(2,2-dimethylpropyl)-1,2,4-triazole
3-(ethylthio)-4-n-octadecyl-5-n-heptyl-1,2,4-triazole
3-(t-octyldithio)-4-n-octadecyl-5-n-tridecyl-1,2,4-triazole
3-(sec.dodecylthio)-4-n-octadecyl-5-n-heptadecyl-1,2,4-triazole
2-methyl-3-(n-octadecylthio)-5-methyl-1,2,4-triazole
2-n-propyl-3-(benzyldithio)-5-ethyl-1,2,4-triazole
2-n-hexyl-3-mercapto-5-(2,2-dimethylpropyl)-1,2,4-triazole
2-n-decyl-3-(cyclohexylthio)-5-n-heptyl-1,2,4-triazole
2-t-dodecyl-3-(ethyldithio)-5-n-tridecyl-1,2,4-triazole
2-n-octadecyl-3-(t-octylthio)-5-n-heptadecyl-1,2,4-triazole
2-n-hexadecyl-3-(ethyldithio)-5-phenyl-1,2,4-triazole
2-n-tetradecyl-3-(sec.-dodecylthio)-5-(4-hydroxyphenyl)-1,2,4-triazole
2-t-octyl-3-(n-octadecyldithio)-5-(3,5-di-t-butyl-4-hydroxyphenyl)-1,2,4-triazole
2-sec.-butyl-3-(cyclohexylthio)-5-(4-t-(butylphenyl)-1,2,4-triazole
2-benzyl-3-(benzyldithio)-5-(4-aminophenyl)-1,2,4-triazole
2-methyl-3-mercapto-5-[4-(N,n-diethylamino)phenyl]-1,2,4-triazole
2-isopropyl-3-(sec.-dodecylthio)-5-(4-chlorophenyl)-1,2,4-triazole 2-sec.-dodecyl-3-(t-octyldithio)-5-(4-methoxyphenyl)-1,2,4-triazole
3-(ethylthio)-4-methyl-5-phenyl-1,2,4-triazole
3-(t-octyldithio)-4-methyl-5-(4-hydroxyphenyl)-1,2,4-triazole
3-(sec.-dodecylthio)-4-methyl-5-(3,5-di-t-butyl-4-hydroxyphenyl)-1,2,4-triazole
3-(n-octadecylthio)-4-methyl-5-(4-t-butylphenyl)-1,2,4-triazole
3-(benzylthio)-4-methyl-5-(4-aminophenyl)-1,2,4-triazole
3-mercapto-4-methyl-5-[4-(N,N-diethylamino)phenyl]-1,2,4-triazole
3-(cyclohexyldithio)-4-methyl-5-(4-chlorophenyl)-1,2,4-triazole
3-(ethyldithio)-4-methyl-5-(4-methoxyphenyl)-1,2,4-triazole
3-(ethyldithio)-4-n-propyl-5-phenyl-1,2,4-triazole
3-(n-octylthio)-4-n-propyl-5-(4-hydroxyphenyl)-1,2,4-triazole
3-(n-dodecyldithio)-4-n-propyl-5-(3,5-di-t-butyl-4-hydroxyphenyl)-1,2,4-triazole
3-(n-octadecylthio)-4-n-propyl-5-(4-t-butylphenyl)-1,2,4-triazole
3-(benzyldithio)-4-n-propyl-5-(4-aminophenyl)-1,2,4-triazole
3-(cyclohexylthio)-4-n-propyl-5-[4-(N,N-diethylamino)phenyl]-1,2,4-triazole
3-(t-octyldithio)-4-n-propyl-5-(4-chlorophenyl)-1,2,4-triazole
3-mercapto-4-n-propyl-5-(4-methoxyphenyl)-1,2,4-triazole
3-(cyclohexyldithio)-4-n-hexyl-5-phenyl-1,2,4-triazole
3-(benzylthio)-4-n-hexyl-5-(4-hydroxyphenyl)-1,2,4-triazole
3-(n-octadecyldithio)-4-n-hexyl-5-(3,5-di-t-butyl-4-hydroxyphenyl)-1,2,4-triazole
3-(sec.dodecylthio)-4-n-hexyl-5-(4-t-butylphenyl)-1,2,4-triazole
3-mercapto-4-n-hexyl-5-(4-aminophenyl)-1,2,4-triazole
3-(t-octyldithio)-4-n-hexyl-5-[4-(N,N-diethylamino)phenyl]-1,2,4-triazole
3-(ethyldithio)-4-n-hexyl-5-(4-chlorophenyl)-1,2,4-triazole
3-(n-dodecyldithio)-4-n-hexyl-5-(4-methoxyphenyl)-1,2,4-triazole
3-(ethylthio)-4-n-octadecyl-5-phenyl-1,2,4-triazole
3-(t-octyldithio)-4-n-octadecyl-5-(4-hydroxyphenyl)-1,2,4-triazole
3-(sec.-dodecylthio)-4-n-octadecyl-5-(3,5-di-t-butyl-4-hydroxyphenyl)-1,2,4-triazole
3-mercapto-4-n-octadecyl-5-(4-t-butylphenyl)-1,2,4-triazole
3-(n-octadecyldithio)-4-n-octadecyl-5-(4-aminophenyl)-1,2,4-triazole
3-(cyclohexyldithio)-4-n-octadecyl-5-(4-chlorophenyl)-1,2,4-triazole
3-(cyclohexylthio)-4-n-octadecyl-5-(4-methoxyphenyl)-1,2,4-triazole
2,5-diphenyl-3-(n-octadecylthio)-1,2,4-triazole
3-(n-octadecyldithio)-4,5-diphenyl-1,2,4-triazole
2-phenyl-3-(n-octadecylthio)-5-(3,5-di-t-butyl-4-hydroxyphenyl)-1,2,4-triazole
3-(n-octadecyldithio)-4-phenyl-5-(3,5-di-t-butyl-4-hydroxyphenyl)-1,2,4-triazole
3-(ethylthio)-5-phenyl-1,2,4-triazole
3-(t-octyldithio)-5-(4-hydroxyphenyl)-1,2,4-triazole
3-(sec.-dodecylthio)-5-(3,5-di-t-butyl-4-hydroxyphenyl)-1,2,4-triazole
3-(n-octadecylthio)-5-(4-t-butylphenyl)-1,2,4-triazole
3-(benzyldithio)-5-(4-aminophenyl)-1,2,4-triazole
3-mercapto-5-[4-(N,N-diethylamino)phenyl]-1,2,4-triazole
3-(cyclohexyldithio)-5-(4-chlorophenyl)-1,2,4-triazole
3-mercapto-5-(4-methoxyphenyl)-1,2,4-triazole
3-(ethyldithio)-4-phenyl-1,2,4-triazole
3-(n-octylthio)-4-(4-methylphenyl)-1,2,4 triazole
3-mercapto-4-(4-isopropylphenyl)-1,2,4-triazole
3-(n-dodecyldithio)-4-(4-bromophenyl)-1,2,4-triazole
3-(n-octadecylthio)-4-(4-ethoxyphenyl)-1,2,4-triazole
3-(benzyldithio)-4-(3,5-di-t-butyl-4-hydroxyphenyl)-1,2,4-triazole
3-(cyclohexylthio)-4-[4-(N-ethylamino)phenyl]-1,2,4-triazole
3-(n-octadecyldithio)-4-phenyl-5-methyl-1,2,4-triazole
3-(sec.-dodecylthio)-4-(4-methylphenyl)-5-methyl-1,2,4-triazole
3-(t-octyldithio)-4-(4-isopropylphenyl)-5-methyl-1,2,4-triazole
3-(ethylthio)-4-(4-bromophenyl)-5-methyl-1,2,4-triazole
3-(benzylthio)-4-(4-ethoxyphenyl)-5-methyl-1,2,4-triazole
3-(cyclohexyldithio)-4-(3,5-di-t-butyl-4-hydroxyphenyl)-5-methyl-1,2,4-triazole
3-(t-octyldithio)-4-[4-(N-ethylamino)phenyl]-1,2,4-triazole
3-(cyclohexylthio)-4-phenyl-5-sec.-butyl-1,2,4-triazole
3-(benzyldithio)-4-(4-methoxyphenyl)-5-sec.-butyl-1,2,4-triazole
3-(n-octadecylthio)-4-(4-isopropylphenyl)-5-sec.-butyl-1,2,4-triazole
3-(n-dodecyldithio)-4-(4-bromophenyl)-5-sec.-butyl-1,2,4-triazole
3-(n-octylthio)-4-(4-ethoxyphenyl)-5-sec.-butyl-1,2,4-triazole
3-(ethyldithio)-4-(3,5-di-t-butyl-4-hydroxyphenyl)-5-sec.-butyl-1,2,4-triazole
3-mercapto-4-[4-(N-ethylamino)phenyl]-5-sec.-butyl-1,2,4-triazole
3-(ethylthio)-4-phenyl-5-n-heptyl-1,2,4-triazole
3-(t-octyldithio)-4-(4-methylphenyl)-5-n-heptyl-1,2,4-triazole
3-(cyclohexyldithio)-4-(4-isopropylphenyl)-5-n-heptyl-1,2,4-triazole
3-(sec.-dodecylthio)-4-(4-bromophenyl)-5-n-heptyl-1,2,4-triazole
3-(n-octadecyldithio)-4-(4-ethoxyphenyl)-5-n-heptyl-1,2,4-triazole
3-(benzylthio)-4-(3,5-di-t-butyl-4-hydroxyphenyl)-5-n-heptyl-1,2,4-triazole
3-(n-octyldithio)-4-[4-(N-ethylaminophenyl)-5-n-heptyl]-1,2,4-triazole
3-(ethyldithio)-4-phenyl-5-heptadecyl-1,2,4-triazole
3-(n-octyldithio)-4-(4-methylphenyl)-5-n-heptadecyl-1,2,4-triazole
3-(n-dodecyldithio)-4-(4-isopropylphenyl)-5-n-heptadecyl-1,2,4-triazole
3-(n-octadecylthio)-4-(4-bromophenyl)-5-n-heptadecyl-1,2,4-triazole 3-mercapto-4-(4-ethoxyphenyl)-5-n-heptadecyl-1,2,4-triazole
3-(cyclohexyldithio)-4-(3,5-di-t-butyl-4-hydroxyphenyl)-5-n-heptadecyl-1,2,4-triazole
3-(benzylthio)-4-[4-(N-ethylamino)phenyl]-5-n-heptadecyl-1,2,4-triazole
3-(ethylthio)-5-benzyl-1,2,4-triazole
3-(t-octyldithio)-4-methyl-5-benzyl-1,2,4-triazole
3-(sec.-dodecylthio)-4-t-butyl-5-benzyl-1,2,4-triazole
3-(n-octadecyldithio-4-n-octyl-5-benzyl-1,2,4-triazole
3-(benzyldithio)-4-n-octadecyl-5-benzyl-1,2,4-triazole
3-(cyclohexyldithio)-4-phenyl-5-benzyl-1,2,4-triazole
3-(n-octadecylthio)-4-(3,5-di-t-butyl-4-hydroxyphenyl)-5-benzyl-1,2,4-triazole
3-(n-dodecyldithio)-4-(4-chlorophenyl)-5-benzyl-1,2,4-triazole
3-(n-octylthio)-4-(4-aminophenyl)-5-benzyl-1,2,4-triazole
3-(ethyldithio)-4-(4-methylphenyl)-5-benzyl-1,2,4-triazole
3-(ethyldithio)-4-benzyl-1,2,4-triazole
3-(n-octylthio)-4-benzyl-5-methyl-1,2,4-triazole
3-(n-dodecyldithio)-4-benzyl-5-sec.-butyl-1,2,4-triazole
3-(n-octadecylthio)-4-benzyl-5-n-nonyl-1,2,4-triazole
3-(benzyldithio)-4-benzyl-5-n-heptadecyl-1,2,4-triazole
3-(cyclohexylthio)-4-benzyl-5-phenyl-1,2,4-triazole
3-(n-octadecyldithio)-4-benzyl-5-(3,5-di-t-butyl-4-hydroxyphenyl)-1,2,4-triazole
3-(n-dodecyldithio)-4-benzyl-5-(4-chlorophenyl)-1,2,4-triazole
3-(n-octylthio)-4-benzyl-5-(4-aminophenyl)-1,2,4-triazole
3-mercapto-4-benzyl-5-(4-methylphenyl)-1,2,4-triazole
3-(cyclohexylthio)-4-(2-pyridyl)-1,2,4-triazole
3-(benzyldithio)-4-(3-pyridyl)-5-methyl-1,2,4-triazole
3-(n-octadecylthio)-4-(4-pyridyl)-5-t-butyl-1,2,4-triazole
3-(n-dodecyldithio)-4-(2-pyridyl)-5-n-octyl-1,2,4-triazole
3-mercapto-4-(3-pyridyl)-5-n-heptadecyl-1,2,4-triazole
3-(n-octylthio)-4-(4-pyridyl)-5-phenyl-1,2,4-triazole
3-(ethyldithio)-4-(2-pyridyl)-5-(3,5-di-t-butyl-4-hydroxyphenyl)-1,2,4-triazole
3-(n-octylthio)-4-(3-pyridyl)-5-(4-aminophenyl)-1,2,4-triazole
3-(n-dodecyldithio)-4-(4-pyridyl)-5-(4-t-butylphenyl)-1,2,4-triazole
3-(n-octadecylthio)-4-(2-pyridyl)-5-benzyl-1,2,4-triazole
3-(n-octadecylthio)-4-(2-piperidyl)-1,2,4-triazole
3-(n-dodecyldithio)-4-(3-piperidyl)-5-methyl-1,2,4-triazole
3-(n-octylthio)-4-(4-piperidyl)-5-t-butyl-1,2,4-triazole
3-(ethylthio)-4-(2-piperidyl)-5-n-octyl-1,2,4-triazole
3-(ethyldithio)-4-(3-piperidyl)-5-n-heptadecyl-1,2,4-triazole
3-mercapto-4-(4-piperidyl)-5-phenyl-1,2,4-triazole
3-(n-dodecyldithio)-4-(2-piperidyl)-5-(3,5-di-t-butyl-4-hydroxyphenyl)-1,2,4-triazole
3-(n-octadecylthio)-4-(3-piperidyl)-5-(4-aminophenyl)-1,2,4-triazole
3-(benzyldithio)-4-(4-piperidyl)-5-(4-t-butylphenyl)-1,2,4-triazole
3-(cyclohexylthio)-4-(2-piperidyl)-5-benzyl-1,2,4-triazole
3-(cyclohexylthio)-4-(2-furyl)-1,2,4-triazole
3-(benzyldithio)-4-(3-furyl)-5-methyl-1,2,4-triazole
3-(n-octadecylthio)-4-(2-furyl)-5-t-butyl-1,2,4-triazole
3-(n-dodecyldithio)-4-(3-furyl)-5-n-octyl-1,2,4-triazole
3-mercapto-4-(2-furyl)-5-n-heptadecyl-1,2,4-triazole
3-(n-octylthio)-4-(3-furyl)-5-phenyl-1,2,4-triazole
3-(ethyldithio)-4-(2-furyl)-5-(3,5-di-t-butyl-4-hydroxyphenyl)-1,2,4-triazole
3-(n-octylthio)-4-(3-furyl)-5-(4-aminophenyl)-1,2,4-triazole
3-(n-dodecylthio)-4-(2-furyl)-5-(4-t-butylphenyl)-1,2,4-triazole
3-(n-octadecyldithio)-4-(3-furyl)-5-benzyl-1,2,4-triazole
3-(n-dodecyldithio)-4-(2-piperidyl)-5-(2-furyl)-1,2,4-triazole
3-(ethylthio)-5-(2-pyridyl)-1,2,4-triazole
3-(t-octyldithio)-4-methyl-5-(3-pyridyl)-1,2,4-triazole
3-(sec.-dodecylthio)-4-n-hexyl-5-(4-pyridyl)-1,2,4-triazole
3-(n-octadecylthio)-4-n-decyl-5-(2-pyridyl)-1,2,4-triazole
3-(n-benzylthio)-4-phenyl-5-(3-pyridyl)-1,2,4-triazole
3-(cyclohexylthio)-4-(3,5-di-t-butyl-4-hydroxyphenyl)-5-(4-pyridyl)-1-2,4-triazole
3-(n-octadecylthio)-4-(4-chlorophenyl)-5-(2-pyridyl)-1,2,4-triazole
3-(n-dodecyldithio)-4-(4-aminophenyl)-5-(2-pyridyl)-1,2,4-triazole
3-(n-octylthio)-4-(4-t-butylphenyl)-5-(3-pyridyl)-1,2,4-triazole
3-(ethyldithio)-4-benzyl-5-(4-pyridyl)-1,2,4-triazole
3-(n-dodecyldithio)-5-(2-pyridyl)-1,2,4-triazole
3-(ethylthio)-4-methyl-5-(2-piperidyl)-1,2,4-triazole
3-(n-octylthio)-4-n-hexyl-5-(3-piperidyl)-1,2,4-triazole
3-mercapto-4-n-decyl-5-(4-piperidyl)-1,2,4-triazole
3-(n-dodecyldithio)-4-phenyl-5-(2-piperidyl)-1,2,4-triazole
3-(n-octadecylthio)-4-(3,5-di-t-butyl-4-hydroxyphenyl)-5-(3-piperidyl)-1,2,4-triazole
3-(benzyldithio)-4-(4-chlorophenyl)-5-(4-piperidyl)-1,2,4-triazole
3-(cyclohexylthio)-4-(4-aminophenyl)-5-(2-piperidyl)-1,2,4-triazole
3-(ethyldithio)-4-(4-t-butylphenyl)-5-(3-piperidyl)-1,2,4-triazole
3-(t-octyldithio)-4-benzyl-5-(4-piperidyl)-1,2,4-triazole
3-(cyclohexyldithio)-5-(2-furyl)-1,2,4-triazole
3-(benzylthio)-4-methyl-5-(3-furyl)-1,2,4-triazole
3-(n-octadecyldithio)-4-n-hexyl-5-(2-furyl)-1,2,4-triazole
3-(n-t-octyldithio)-4-n-decyl-5-(3-furyl)-1,2,4-triazole
3-(ethylthio)-4-phenyl-5-(2-furyl)-1,2,4-triazole
3-mercapto-4-(3,5-di-t-butyl-4-hydroxyphenyl)-5-(3-furyl)-1,2,4-triazole
3-(benzyldithio)-4-(4-chlorophenyl)-5-(2-furyl)-1,2,4-triazole
3-(cyclohexylthio)-4-(4-aminophenyl)-5-(3-furyl)-1,2,4-triazole
3-(benzylthio)-4-(4-t-butylphenyl)-5-(2-furyl)-1,2,4-triazole
3-(cyclohexyldithio)-4-benzyl-5-(3-furyl)-1,2,4-triazole 3-mercapto-4-cyclohexyl-1,2,4-triazole
3-(ethyldithio)-4-cyclohexyl-5-methyl-1,2,4-triazole
3-(n-octylthio)-4-cyclohexyl-5-t-butyl-1,2,4-triazole
3-(n-dodecyldithio)-4-cyclododecyl-5-n-octyl-1,2,4-triazole
3-(n-octadecylthio)-4-cyclododecyl-5-n-heptadecyl-1,2,4-triazole
3-(benzyldithio)-4-cyclododecyl-5-phenyl-1,2,4-triazole
3-(cyclohexylthio)-4-cyclopropyl-5-(3,5-di-t-butyl-4-hydroxy-phenyl)-1-2,4-triazole
3-(n-octadecyldithio)-4-cyclopropyl-5-(4-chloro-phenyl)-1,2,4-triazole
3-(sec-dodecylthio)-4-cyclopropyl-5-(4-amino-phenyl)-1,2,4-triazole
3-(t-octyldithio)-4-cyclohexyl-5-(4-t-butylphenyl)-1,2,4-triazole
3-(ethylthio)-4-cyclohexyl-5-benzyl-1,2,4-triazole
3-(n-octylthio)-4-cyclopropyl-5-(4-pyridyl)-1,2,4-triazole
3-(n-dodecyldithio)-4-cyclohexyl-5-(3-piperidyl)-1,2,4-triazole
3-(n-octylthio)-4-cyclododecyl-5-(2-furyl)-1,2,4-triazole
3-mercapto-5-cyclododecyl-1,2,4-triazole
3-(ethyldithio)-4-methyl-5-cyclododecyl-1,2,4-triazole
3-(n-octylthio)-4-t-butyl-5-cyclododecyl-1,2,4-triazole
3-(n-dodecyldithio)-4-n-octyl-5-cyclododecyl-1,2,4-triazole
3-(n-octadecylthio)-4-n-heptadecyl-5-cyclopropyl-1,2,4-triazole
3-(benzyldithio)-4-phenyl-5-cyclopropyl-1,2,4-triazole
3-(cyclohexylthio)-4-(3,5-di-t-butyl-4-hydroxy-phenyl)-5-cyclopropyl-1,2,4-triazole
3-(n-octadecyldithio)-4-(4-chlorophenyl)-5-cyclohexyl-1,2,4-triazole
3-(sec-dodecylthio)-4-(4-aminophenyl)-5-cyclohexyl-1,2,4-triazole
3-(t-octyldithio)-4-(t-butylphenyl)-5-cyclohexyl-1,2,4-triazole
3-(ethylthio)-4-benzyl-5-cyclohexyl-1,2,4-triazole
3-(n-octylthio)-4-(2-pyridyl)-5-cyclododecyl-1,2,4-triazole
3-(n-dodecyldithio)-4-(4-piperidyl)-5-cyclopropyl-1,2,4-triazole
3-(n-octyldithio)-4-(3-furyl)-5-cyclohexyl-1,2,4-triazole
p-phenylenebis(4-mercapto-5-phenyl-2,3,5-triazole)
bis[4-(n-dodecyldithio)-5-n-butyl-2,3,5-triazolyl]-1',4'-cyclohexane
1',4'-tetramethylenebis[4-(t-octyldithio)-5-methyl-2,3,5-triazole]
1',8'-octamethylenebis[4-(n-dodecylthio)-5-phenyl-2,3,5-triazole]
1',12'-dodecamethylenebis[4-mercapto-2,3,5-triazole]
bis[4-(benzyldithio)-2,3,5-triazolyl]-3',4'-furan
1',6'-hexamethylenebis(4-phenyl-2,3,5-triazole-1-dithiyl)
1',12'-dodecamethylenebis(4-phenyl-5-methyl-2,3,5-triazole-1-dithiyl)
methylenebis(4-n-hexyl-5-methyl-2,3,5-triazole-1-thiyl)
bis[4-n-dodecyl-5-methyl-2,3,5-triazole-1-thiyl]-1',4'-cyclohexane
bis[4-cyclohexyl-5-n-butyl-2,3,5-triazole-1-thiyl]-2',5'-thiophene
n-octadecylammonium 4-methyl-5-phenyl-1,2,4-triazole-3-thiolate
n-decylammonium 5-phenyl-1,2,4-triazole-3-thiolate
N,N-di-n-decylammonium 4-phenyl-5-n-hexyl-1,2,4-triazole-3-thiolate
1-phenyl-3-mercapto-5-methyl-1,2,4-triazole
1-(3,5-di-t-butyl-4-hydroxyphenyl)-3-(n-propylthio)-5-n-butyl-1,2,4-triazole
1-cyclohexyl-3-(sec-dodecyldithio)-5-n-propyl-1,2,4-triazole
1-n-octyl-3-(n-octadecyldithio)-5-cyclohexyl-1,2,4-triazole
1-n-decyl-3-(n-octylthio)-5-n-hexyl-1,2,4-triazole
1-n-butyl-3-(n-dodecylthio)-5-(2-pyridyl)-1,2,4-triazole
1-phenyl-3-(benzyldithio)-5-n-dodecyl-1,2,4-triazole The lubricating compositions of the present invention are non-corrosive to metals, e.g. copper, silver, copper alloys, silver alloys and similar metals which may come into contact with them. Moreover, the lubricant compositions inhibit the corrosion of such metals and alloys caused by sulphur and/or corrosive sulphur-containing organic compounds present in the lubricant compositions. Some of the lubricating compositions of the invention exhibit improved antiwear, antioxidant and metal deactivating properties.

The following Examples further illustrate the present invention. Parts and percentages are by weight unless otherwise stated. Parts by weight bear the same relation to parts by volume as do kilograms to liters.

EXAMPLES 1 TO 16

Compounds of formula I wherein R" is H and x is 1

EXAMPLE 1

A mixture of 97.8 parts of 1-heptanoyl-4-methyl-3-thiosemicarbazide, 18.0 parts of sodium hydroxide pellets and 500 parts by volume of water was heated at reflux temperature for two hours. The reaction mixture was cooled and the product precipitated by neutralising with concentrated hydrochloric acid. This was then filtered, dried and recrystallised from absolute ethanol resulting in an 83 percent yield of 3-metcapto-4-methyl-5-n-hexyl-1,2,4-triazole. The product had a melting point of 83.5°–84.5° C. and the following elemental analysis.

Found: C-53.80%, H-8.64%, N-21.12%, S-16.06%:
Calculated: C-54.23%, H-8.60%, N-21.09%, S-16.09%.

The compound exhibited excellent corrosion inhibiting properties when incorporated in a lubricating oil.

Further examples (2 to 16) are listed in Table I and these were prepared in a similar manner to Example 1.

TABLE 1

| Example | Product | Yield (%) | Melting point (°C.) | Elemental analysis (percentage by weight) |
|---|---|---|---|---|
| 2 | 3-mercapto-5-phenyl-1,2,4-triazole | 72 | 257–260 | Found: C-54.87 H-4.04 N-23.41 S-16.44 |
| | | | | Calculated: C-54.22 H-3.98 N-23.72 S-18.08 |

TABLE 1-continued

| Example | Product | Yield (%) | Melting point (°C.) | Elemental analysis (percentage by weight) |
|---|---|---|---|---|
| 3 | 3-mercapto-5-(4-t-butylphenyl)-1,2,4,-triazole | 67 | 289–290 | Found: C-61.87 H-6.70 N-18.00 S-13.95<br>Calculated: C-61.76 H-6.48 N-18.01 S-13.74 |
| 4 | 3-mercapto-5-(4-hydroxyphenyl)-1,2,4-triazole | 53 | 324–325 (dec.) | Found: C-49.52 H-3.70 N-21.68 S-16.89<br>Calculated: C-49.73 H-3.65 N-21.75 S-16.59 |
| 5 | 2-nethyl-3-mercapto-5-n-hexyl-1,2,4-triazole | 21 | 54–56 | Found: C-54.95 H-8.91 N-20.78 S-15.76<br>Calculated: C-54.23 H-8.60 N-21.09 S-16.09 |
| 6 | 2-methyl-3-mercapto-5-phenyl-1,2,4-triazole | 52 | 263–266 | Found: C-56.65 H-4.94 N-22.08 S-16.49<br>Calculated: C-56.52 H-4.74 N-21.98 S-16.76 |
| 7 | 3-mercapto-4-methyl-5-phenyl-1,2,4-triazole | 91 | 168–169 | Found: C-56.38 H-4.82 N-21.87 S-16.80<br>Calculated: C-56.52 H-4.74 N-21.98 S-16.76 |
| 8 | 3-mercapto-4-methyl-5-n-heptadecyl-1,2,4-triazole | 66 | 97–99 | Found: C-61.52 H-10.58 N-10.73 S-7.69<br>Calculated for $C_{20}H_{39}N_3S \cdot 2H_2O$ C-61.65 H-11.12 N-10.79 S-8.24 |
| 9 | 3-mercapto-4-ethyl-5-n-hexyl-1,2,4-triazole | 99 | 65–67 | Found: C-56.64 H-8.99 N-19.31 S-14.84<br>Calculated: C-56.29 H-8.98 N-19.70 S-15.03 |
| 10 | 3-mercapto-5-methyl-1,2,4-triazole | 38 | 272–275 | Found: C-30.99 H-4.42 N-36.19 S-27.99<br>Calculated: C-31.28 H-4.38 N-36.49 S-27.85 |
| 11 | 3-mercapto-4,5-dimethyl-1,2,4-triazole | 37 | 214 | Found: C-36.09 H-5.34 N-31.64 S-24.89<br>Calculated: C-37.19 H-5.46 N-32.53 S-24.82 |
| 12 | 3-mercapto-4-phenyl-5-methyl-1,2,4-triazole | 48 | 222–224 | Found: C-56.58 H-4.86 N-21.83 S-16.27<br>Calculated: C-56.52 H-4.74 N-21.98 S-16.76 |
| 13 | 3-mercapto-4-methyl-1,2,4-triazole | 77 | 116–118 | Found: C-31.35 H-4.22 N-36.65 S-27.83<br>Calculated: C-31.29 H-4.38 N-36.50 S-27.84 |
| 14 | 3-mercapto-5-hexyl-1,2,4-triazole | 97 | 189–190 | Found: C-51.78 H-8.44 N-22.54 S-17.19<br>Calculated: C-51.85 H-8.16 N-22.68 S-17.30 |
| 15 | p-phenylenebis(4-mercapto-5-phenyl-2,3,5-triazole) | 68 | >350 | Found: C-60.56 H-3.94 N-19.12 S-14.74<br>Calculated: C-61.66 H-3.76 N-19.62 S-14.96 |
| 16 | 1',8'-octamethylenebis(4-mercapto-5-methyl-2,3,5-triazole) | 93 | 269–272 | Found: C-49.10 H-7.31 N-24.41 S-19.02<br>Calculated: C-49.38 H-7.11 N-24.67 S-18.83 |

EXAMPLES 17–25

Compounds of formula I wherein R" is other than H and x is 2

[New compositions of matter]

EXAMPLE 17

2.3 parts of sodium metal were added to 100 parts by volume of methyl alcohol with cooling to maintain an internal temperature of 45° to 55° C. 191 parts of 3-mercapto-4-methyl-5-phenyl-1,2,4-triazole were added and this dissolved to form a clear solution. The reaction mixture was cooled to 10° C. and a solution of 28.1 parts of n-dodecylsulphenylbromide in 73 parts by volume of carbon tetrachloride was added over 45 minutes, the reaction temperature being maintained at 10° C. by cooling. The mixture was stirred at 10° C. for a further hour. After washing with water (5×100 parts by volume) the carbon tetrachloride/methyl alcohol solution was dried with anhydrous sodium sulphate, filtered and the solvent removed using a rotary evaporator. The resulting solid was recrystallised from hexane/carbon tetrachloride yielding 34 percent of 3-(n-dodecyldithio)-4-methyl-5-phenyl-1,2,4-triazole which had a melting point of 78°–81° C. and the following elemental analysis:

Found: C-64.12%, H-8.48%, N-11.07%, S-16.38%:
Calculated: C-64.41%, H-8.49%, N-10.73%, S-16.37%.

This compound, when incorporated into a lubricating oil, exhibited excellent corrosion inhibiting and metal passivating properties.

Further Examples (18–25) are listed in Table II and these were prepared in a similar manner to Example 17.

TABLE II

| Example | Product | Yield (%) | Melting point (°C.) | Elemental analysis (percentage by weight) |
|---|---|---|---|---|
| 18 | 3-(n-dodecyldithio)-5-phenyl-1,2,4-triazole | 50 | 52.0–57.0 | Found: C-63.35 H-8.09 N-11.08 S-16.26<br>Calculated: C-63.61 H-8.28 N-11.13 S-16.98 |
| 19 | 3-(n-dodecyldithio)-5-n-hexyl-1,2,4-triazole | 34 | 45.5–46.5 | Found: C-62.51 H-10.06 N-10.32 S-16.93<br>Calculated: C-62.29 H-10.19 N-10.90 S-16.63 |
| 20 | 3-(n-dodecyldithio)-1,2,4-triazole | 23 | 71.5–72.5 | Found: C-55.80 H-9.20 N-13.72 S-21.17<br>Calculated: C-55.77 H-9.03 N-13.94 S-21.27 |
| 21 | 3-(n-dodecyldithio)-5-methyl-1,2,4-triazole | 49 | 98.0–99.0 | Found: C-57.18 H-9.26 N-13.27 S-20.31<br>Calculated: C-57.08 H-9.24 N-13.32 S-20.32 |
| 22 | 3-(n-dodecyldithio)-4-methyl-1,2,4-triazole | 35 | 54.0–56.0 | Found: C-57.20 H-9.26 N-13.56 S-20.38<br>Calculated: C-57.08 H-9.24 N-13.32 S-20.32 |
| 23 | 3-(n-dodecyldithio)-4,5-dimethyl-1,2,4-triazole | 17 | 57.0–58.0 | Found: C-58.45 H-9.39 N-13.00 S-19.16<br>Calculated: C-58.31 H-9.48 N-12.75 S-19.46 |
| 24 | 3-(n-dodecyldithio)-4-phenyl-5-methyl-1,2,4-triazole | 34 | 49.5–50.5 | Found: C-64.79 H-8.46 N-11.10 S-16.50<br>Calculated: C-64.40 H-8.49 N-10.73 S-16.37 |
| 25 | 1,1'-dithiobis(4-n-hexyl-2,3,5-triazole) | 23 | 126.0–127.0 | Found: C-52.11 H-7.76 N-22.71 S-17.12<br>Calculated: C-52.13 H-7.66 N-22.81 S-17.40 |

EXAMPLE 26

Compounds of Formula I wherein R is other than H and x is 1

A mixture of 11.7 parts of 3-mercapto-5-(4-tert.-butylphenyl)-1,2,4-triazole, 12.5 parts of 1-bromododecane and 100 parts by volume of ethyl alcohol was heated at reflux temperature for four hours. After cooling to 20° C., a four percent weight/volume aqueous sodium hydroxide solution was added followed by 100 parts by volume of water. The precipitated product was filtered and dried yielding 59 percent of 3-(n-dodecylthio)-5-(4-tert.butylphenyl)-1,2,4-triazole which had a melting point of 87°-92° and the following elemental analysis:

Found: C-71.40%, H-9.75%, N-9.92%, S-8.03%: Calculated: C-71.77%, H-9.79%, N-10.46%, S-7.98%.

The compound, when incorporated into a lubricating oil, exhibited excellent corrosion inhibiting properties.

Further Examples (27–42) are listed in Table III and these were prepared in a similar manner to Example 26.

ethyl alcohol and dried, yielding 61 percent of N,N-di-n-butylammonium 5-phenyl-1,2,4-triazole-3-thiolate which had a melting point of 133°-137° C. and the following elemental analysis:

Found: C-62.79%, H-8.55%, N-18.60%, S-10.70%: Calculated: C-62.69%, H-8.55%, N-18.60%, S-10.46%.

Similarly prepared was a tertiary alkylammonium 5-phenyl-1,2,4-triazole-3-thiolate (Example 44) in which the tertiary alkylammonium species was derived from a commercial mixture of primary amines of carbon number tertiary $C_{18}$ to tertiary $C_{22}$. The product was a sticky wax at 23° C. and had the following elemental analysis Found: C-70.16%, H-10.80%, S-6.37%: Calculated for $C_{28}H_{50}N_4S$: C-70.83%, H-10.62%, S-6.75%.

Each of these compounds exhibited excellent metal passivating properties when incorporated into a lubricating oil.

EXAMPLES 45–60

In order to evaluate the corrosion inhibiting performance of the lubricant compositions, a bearing corro-

TABLE III

| Example | Product | Yield (%) | Melting point (°C.) | Elemental (percent by weight) | |
|---|---|---|---|---|---|
| 27 | 3-(n-dodecylthio)-1,2,4-triazole | 59 | 79–82 | Found: | C-62.54 H-10.42 N-15.42 S-11.71 |
| | | | | Calculated: | C-62.40 H-10.10 N-15.60 S-11.90 |
| 28 | 3-(n-dodecylthio)-4-methyl-1,2,4-triazole | 21 | 60–62 | Found: | C-64.46 H-10.59 N-14.59 S-10.87 |
| | | | | Calculated: | C-63.55 H-10.31 N-14.83 S-11.31 |
| 29 | 3-(n-dodecylthio)-5-phenyl-1,2,4-triazole | 71 | 71–74 | Found: | C-69.03 H- 9.05 N-11.36 S- 8.93 |
| | | | | Calculated: | C-69.51 H- 9.04 N-12.16 S- 9.28 |
| 30 | 3-(n-dodecylthio)-5-n-hexyl-1,2,4-triazole | 58 | 63–64 | Found: | C-68.01 H-10.80 N-11.66 S- 8.85 |
| | | | | Calculated: | C-67.93 H-11.12 N-11.89 S- 9.07 |
| 31 | 2-methyl-3-(n-dodecylthio)-5-phenyl-1,2,4-triazole | 59 | 24–29 | Found: | C-67.86 H- 9.64 N-10.34 S- 7.94 |
| | | | | Calculated for $C_{21}H_{22}N_3S$. $C_2H_5OH$ | C-68.09 H- 9.69 N-10.36 S- 7.91 |
| 32 | 3-(n-dodecylthio)-4-methyl-5-phenyl-1,2,4-triazole | 63 | 95–98 | Found: | C-70.27 H- 9.69 N-11.42 S- 9.15 |
| | | | | Calculated: | C-70.14 H- 9.25 N-11.69 S- 8.92 |
| 33 | 3-(n-dodecylthio)-4-methyl-5-n-hexyl-1,2,4-triazole | 56 | 55–56 | Found: | C-68.08 H-11.18 N-11.14 S- 8.71 |
| | | | | Calculated: | C-68.60 H-11.24 N-11.43 S- 8.72 |
| 34 | 3-(n-dodecylthio)-1,2,4-triazole | 59 | 79–82 | Found: | C-62.54 H-10.42 N-15.42 S-11.71 |
| | | | | Calculated: | C-62.40 H-10.10 N-15.60 S-11.90 |
| 35 | 2-methyl-3-(n-dodecylthio)-1,2,4-triazole | 66 | 101–103 | Found: | C-63.85 H-10.36 N-14.66 S-11.33 |
| | | | | Calculated: | C-63.55 H-10.31 N-14.83 S-11.31 |
| 36 | 3-(n-dodecylthio)-4-ethyl-5-n-hexyl-1,2,4-triazole | 81 | LIQUID | Found: | C-66.53 H-11.33 N- 9.93 S- 7.67 |
| | | | | Calculated for $C_{22}H_{43}N_3S$. $H_2O$ | C-66.10 H-11.35 N-10.52 S- 8.02 |
| 37 | 3-(methoxycarbonylmethylthio)-4-methyl-5-n-hexyl-1,2,4-triazole | 37 | LIQUID | Found: | C-52.73 H- 7.84 N-15.92 S-11.89 |
| | | | | Calculated: | C-53.11 H- 7.80 N-15.49 S-11.81 |
| 38 | 3-(n-dodecylthio)-4-phenyl-1,2,4-triazole | 74 | 42.5–43.5 | Found: | C-57.18 H- 9.24 N-13.27 S-20.31 |
| | | | | Calculated: | C-57.08 H- 9.26 N-13.32 S-20.32 |
| 39 | 1',10'-decamethylenebis(4-n-hexyl-5-methyl-2,3,5-triazole-1-thiyl) | 50 | 108–110 | Found: | C-62.85 N- 9.78 N-15.60 S-11.99 |
| | | | | Calculated: | C-62.64 H- 9.76 N-15.66 S-11.94 |
| 40 | 1',8'-octamethylenebis[4-(n-dodecylthio)-5-methyl-2,3,5-triazole] | 72 | 102–106 | Found: | C-67.45 H-10.56 N-11.93 S- 9.02 |
| | | | | Calculated: | C-67.40 H-10.72 N-12.41 S- 9.47 |
| 41 | 3,5-bis(n-dodecylthio)-4-methyl-1,2,4-triazole | 38 | 68–70 | Found: | C-66.97 H-11.15 N- 8.51 S-13.21 |
| | | | | Calculated: | C-67.02 H-11.04 N- 8.69 S-13.25 |
| 42 | 3,5-bis(n-dodecylthio)-1,2,4-triazole | 35 | 81–83 | Found: | C-66.39 H-10.64 N- 8.69 S-13.75 |
| | | | | Calculated: | C-66.46 H-10.94 N- 8.95 S-13.65 |

EXAMPLES 43 AND 44

Amine salts of compounds of formula I wherein R" is H and x is 1

A mixture of 17.7 parts of 3-mercapto-5-phenyl-1,2,4-triazole, 12.9 parts of di-n-butylamine and 50 parts by volume of ethyl alcohol was heated at reflux temperature for one and a half hours. On cooling to 23° C., the product precipitated and this was filtered, washed with sion rig described by Staudt et al (SAE 680538) was used to determine the bearing weight loss and colour change of Petter W.1. copper/lead bearings, under the conditions set out below.

The results obtained are set out in Table IV. For the purposes of comparison, data are included relating to a control experiment using no additive and a further run using a commercial additive.

TABLE IV

| Example | Additive | Concentration (% w/w) | Cu/Pb Bearing Colour | Bearing weight loss (mg) |
|---|---|---|---|---|
| | None | — | 3 | 5.0 |
| | A commercial 2.5-dialkyldithio-1,3,4-thiadiazole "Amoco 150" | 0.1 | 2+ | 12.0 |
| | | 0.2 | 2 | 4.6 |
| | | 0.5 | 1+ to 2 | 2.0 |
| 45 | 3-(n-dodecylthio)-5-(4-t-butyl-phenyl)-1,2,4-triazole | 0.5 | 1 | 10.5 |
| 46 | 3-(n-dodecylthio)-4-methyl-5-n-hexyl-1,2,4-triazole | 0.5 | 0 to 1 | 12.5 |
| 47 | 3-(n-dodecyldithio)-5-phenyl-1,2-4-triazole | 0.2 | 0 to 1 | 3.5 |
| 48 | 3-(n-dodecyldithio)-4-methyl-5-phenyl-1,2,4-triazole | 0.1 | 1 | 11.9 |
| 49 | 3-mercapto-4-methyl-5-n-hexyl-1,2,4-triazole | 0.01 | 0 to 1 | 15.3 |
| 50 | 1',10'-decamethylenebis[4-n-hexyl-5-methyl-2,3,5-triazole-1-thiyl] | 0.1 | 1+ | 6.5 |
| 51 | 1',8'-octamethylenebis[4-(dodecylthio)-5-methyl-2,3,5-triazole | 0.1 | 1+ | 9.5 |
| 52 | 3-(n-dodecyldithio)-4-methyl-1,2,4-triazole | 0.1 | 1 to 2 | 3.4 |
| 53 | 3-(n-dodecylthio)-4-methyl-1,2,4-triazole | 0.1 | 0 | 6.4 |
| 54 | 3-(n-dodecyldithio)-4,5-dimethyl-1,2,4-triazole | 0.1 | 1+ | 1.6 |

The above tests are run in "Catenex 41" an SAE 30 grade oil containing 1 percent weight/volume of "Lubrizol 1395", a zinc dialkyldithiophosphate extreme pressure/antiwear additive and 5 percent weight/weight of "Lubrizol 894", a polyamine dispersant, at a temperature of 150° C.

In considering the results it should be borne in mind that a bearing colour of 0=clean and 3=black, a bearing weight of <16 mg represents a "pass". Bearing weight loss and colour should not be considered in isolation. Similar results were obtained for the following Examples:

EXAMPLE 55
3-(n-dodecylthio)-5-phenyl-1,2,4-triazole.

EXAMPLE 56
2-methyl-3-(n-dodecylthio)-5-phenyl-1,2,4-triazole.

EXAMPLE 57
3-(n-dodecylthio)-5-n-hexyl-1,2,4-triazole.

EXAMPLE 58
3-(n-dodecylthio)-1,2,4-triazole.

EXAMPLE 59
3-(n-dodecylthio)-5-methyl-1,2,4-triazole.

EXAMPLE 60
3-(n-dodecyldithio)-4-phenyl-5-methyl-1,2,4-triazole.

The results in Table IV demonstrate the effectiveness of the compositions of the invention relative to existing commercial products. The performance of the compositions of Examples 47, 48 and 53 is particularly impressive in view of the low concentration levels of the additive used.

EXAMPLES 61 to 68

In order to evaluate the metal passivating performance of the lubricant compositions, the additives in Table V were subjected to copper strip corrosion tests as described below.

Copper Strip I Test

A sample of bright copper measuring 7.62 cm×1.27 cm×0.16 cm was totally immersed in 50 ml of aromatic spindle oil containing 50 parts per million of elemental sulphur and one of the additives listed in Table V, for three hours at 100° C.

At the end of the test, the strip was removed from the oil, washed with petroleum ether, dried and examined visually for corrosion in comparison with the ASTM D130 corrosion standard.

Copper Strip II Test

After washing the sample of copper which had undergone the Copper Strip I Test it was placed in another 50 ml sample of aromatic spindle oil containing 50 parts per million of elemental sulphur but none of the additives listed in Table V.

At the end of the test the strip was removed from the oil, washed with petroleum ether, dried and examined visually for corrosion, in comparison with the ASTM D 130 corrosion standard.

In Table V, an ASTM rating of four indicates very heavy black tarnishing whereas a rating of one indicates only slight tarnishing.

TABLE V

| Example | Additive | Concentration (% w/w) | Copper Strip I Test | Copper Strip II Test |
|---|---|---|---|---|
| | None | — | 4c | 4c |
| | A commercial 2,5-dialkyldithio-1,3,4-thiadiazole (Amoco 150) | 0.05 | 3a | 3b |
| | | 0.20 | 1a to 1b | 3b |
| 61 | 3-(n-dodecyldithio)-5-phenyl-1,2,4-triazole | 0.05 | 1b | 1c |

TABLE V-continued

| Example | Additive | Concentration (% w/w) | Copper Strip I Test | Copper Strip II Test |
|---|---|---|---|---|
| 62 | 3-(n-dodecyldithio)-4-methyl-5-phenyl-1,2,4-triazole | 0.05 | 1b | 1a |
| 63 | di-n-butylammonium-5-phenyl-1,2,4-triazole-3-thiolate | 0.05 | 1a | 1a to 1b |
| 64 | 3-(n-dodecyldithio)-1,2,4-triazole | 0.05 | 2a | 2a |
| 65 | 3-(n-dodecyldithio)-5-methyl-1,2,4-triazole | 0.2 | 1a | 1a |
| 66 | 3-(n-dodecyldithio)-4-methyl-1,2,4-triazole | 0.2 | 1a | 1a |
| 67 | 3-(n-dodecyldithio)-4,5-dimethyl-1,2,4-triazole | 0.2 | 1a | 1a |
| 68 | 3-(n-dodecyldithio)-4-phenyl-5-methyl-1,2,4-triazole | 0.2 | 1a | 1a |

The results in Table V demonstrate the high degree of effectiveness of the compositions of the invention in passivating copper.

What is claimed is:

1. A lubricant composition comprising a major proportion of an oil of lubricating viscosity and from 0.001 to 10% by weight, based on the total composition, of a compound of the formula

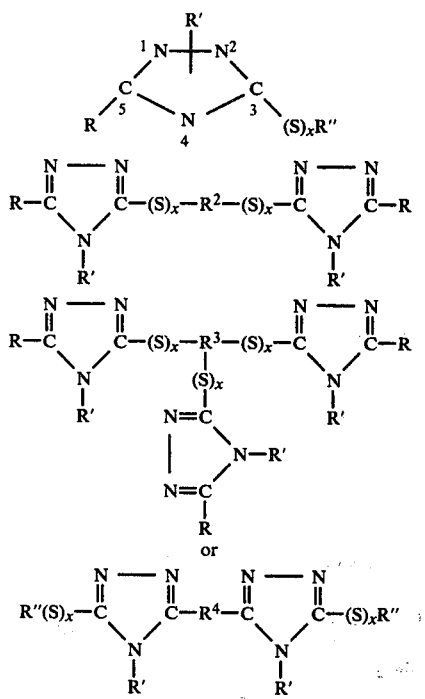

wherein X is an integer from 1 to 25; R, R' and R" are the same or different and each is hydrogen, a straight- or branched-chain alkyl having 1 to 20 carbon atoms; or said alkyl substituted by one or more halogen atoms or alkoxy groups having 1 to 12 carbon atoms; a straight- or branched-chain alkenyl having 2 to 12 carbon atoms; a straight- or branched-chain alkynyl having 2 to 12 carbon atoms; cycloalkyl having 3 to 12 carbon atoms; aryl having 6 to 10 carbon atoms; aralkenyl having 8 to 12 carbon atoms; aralkynyl having 8 to 12 carbon atoms; aralkyl having 7 to 20 carbon atoms; piperidyl, pyridyl; furyl; or said cycloalkyl, aryl, aralkenyl, aralkynyl, aralkyl, piperidyl, pyridyl or furyl substituted by one or more straight or branched alkyl having from 1 to 12 carbon atoms which alkyl groups may be substituted by halogen atoms, by alkoxy having 1 to 12 carbon atoms, by alkylthio having 1 to 18 carbon atoms, by alkylamino having 1 to 24 carbon atoms, by dialkylamino having 1 to 24 carbon atoms, by hydroxy, by cyano or by mixtures of said substituents; or R is the group —$(S)_xR''$;

or when R and R' are different from R", (a) R" can be

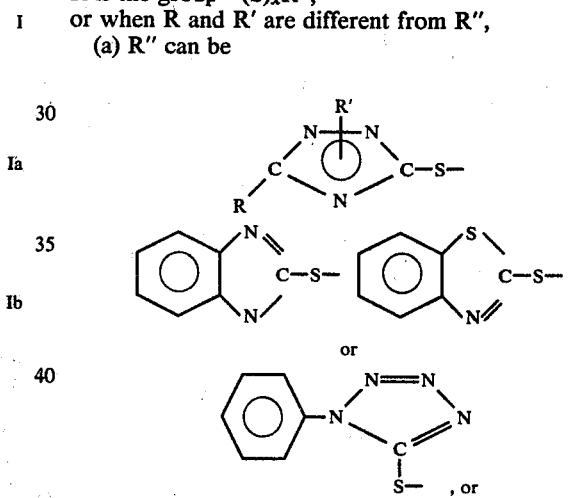

(b) R" is the ammonium cation or a quaternary ammonium cation having 2 to 22 carbon atoms;

$R^2$ is

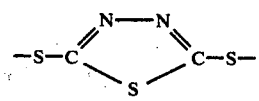

$R^3$ is

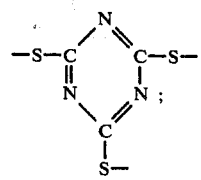

or $R^2$ and $R^4$ are alkylene having 1 to 12 carbon atoms; cycloalkylene having 5 to 12 carbon atoms, arylene having 6 to 10 carbon atoms, furandiyl or thiophenediyl.

2. A composition as claimed in claim 1 wherein the amount of compound I, Ia, Ib or Ic is from 0.01% to 5% by weight, based on the total lubricant composition.

3. A composition as claimed in claim 1 wherein R is a group—$(S)_xR''$ and x is 1.

4. A composition as claimed in claim 1 wherein the lubricating oil component is a mineral oil.

5. A compound having the formula

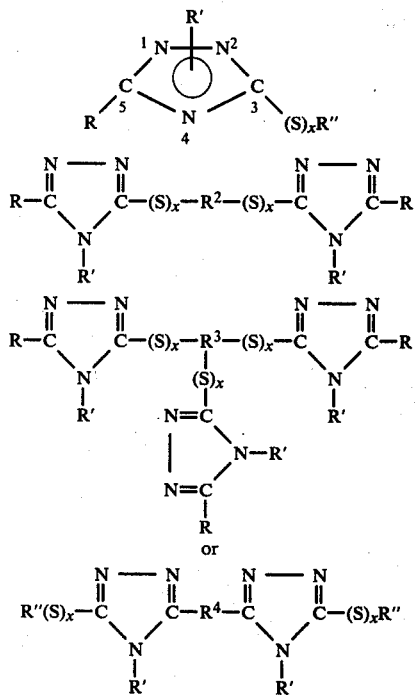

wherein x is an integer from 2 to 25; R, R' and R'' are the same or different and each is hydrogen, a straight- or branched-chain alkyl having 1 to 20 carbon atoms; or said alkyl substituted by one or more halogen atoms or alkoxy groups having 1 to 12 carbon atoms; a straight- or branched-chain alkenyl having 2 to 12 carbon atoms; a straight- or branched-chain alkynyl having 2 to 12 carbon atoms; cycloalkyl having 3 to 12 carbon atoms; aryl having 6 to 10 carbon atoms; aralkenyl having 6 to 12 carbon atoms; aralkynyl having 8 to 12 carbon atoms; aralkyl having 7 to 20 carbon atoms; piperidyl, pyridyl; furyl; or said cycloalkyl, aryl, aralkenyl, aralkynyl, aralkyl, piperidyl, pyridyl or furyl substituted by one or more straight or branched alkyl having from 1 to 12 carbon atoms which alkyl groups may be substituted by halogen atoms, by alkoxy having 1 to 12 carbon atoms, by alkylthio having 1 to 18 carbon atoms, by alkylamino having 1 to 24 carbon atoms, by dialkylamino having 1 to 24 carbon atoms, by hydroxy, by cyano or by mixtures of said substituents; or R is the group—$(S)_xR''$;

or when R and R' are different from R'', (a) R'' can be

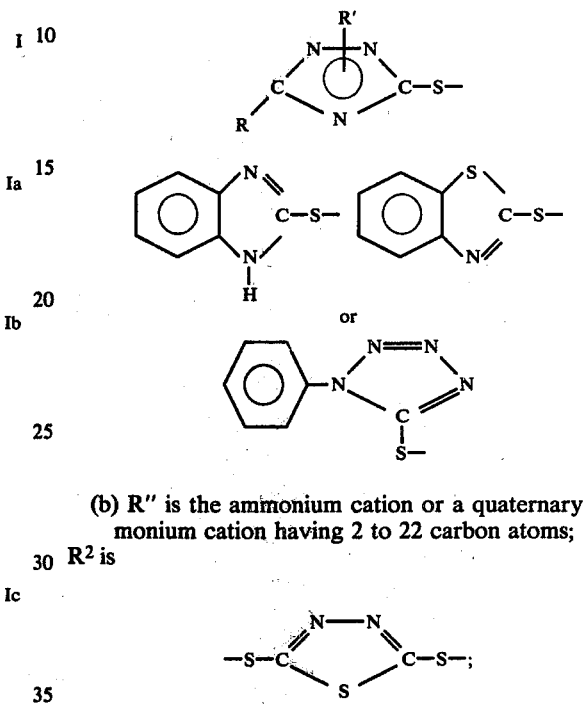

(b) R'' is the ammonium cation or a quaternary ammonium cation having 2 to 22 carbon atoms;

$R^2$ is

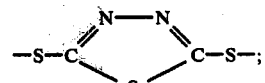

$R^3$ is

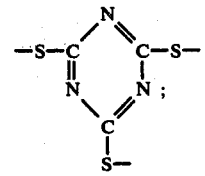

or $R^2$ and $R^4$ are alkylene having 1 to 12 carbon atoms; cycloalkylene having 5 to 12 carbon atoms, arylene having 6 to 10 carbon atoms, furandiyl or thiophenediyl.

6. A compound as claimed in claim 5 wherein R is a group—$(S)_xR''$ and x is 1.

* * * * *